US008822718B2

(12) United States Patent  
Bock et al.

(10) Patent No.: US 8,822,718 B2
(45) Date of Patent: Sep. 2, 2014

(54) PROCESS FOR PREPARING ISOCYANATES BY THERMALLY CLEAVING CARBAMATES

(75) Inventors: Michael Bock, Ruppertsberg (DE); Eckhard Stroefer, Mannheim (DE); Robert Baumann, Mannheim (DE); Axel Franzke, Mannheim (DE); Joachim Pfeffinger, Ludwigshafen (DE)

(73) Assignee: BASF SE, Ludwigshafen (DE)

( * ) Notice: Subject to any disclaimer, the term of this patent is extended or adjusted under 35 U.S.C. 154(b) by 70 days.

(21) Appl. No.: 13/513,460

(22) PCT Filed: Nov. 30, 2010

(86) PCT No.: PCT/EP2010/068500
§ 371 (c)(1),
(2), (4) Date: Jun. 1, 2012

(87) PCT Pub. No.: WO2011/067242
PCT Pub. Date: Jun. 9, 2011

(65) Prior Publication Data
US 2012/0245377 A1   Sep. 27, 2012

(30) Foreign Application Priority Data

Dec. 1, 2009  (EP) .................................. 09177643

(51) Int. Cl.
*C07C 263/04*   (2006.01)

(52) U.S. Cl.
USPC ......................................................... 560/345

(58) Field of Classification Search
None
See application file for complete search history.

(56) References Cited

U.S. PATENT DOCUMENTS

| | | | |
|---|---|---|---|
| 3,743,941 A | 7/1973 | Gans et al. | |
| 3,919,278 A * | 11/1975 | Rosenthal et al. | ............ 560/345 |
| 4,482,499 A | 11/1984 | Merger et al. | |
| 4,692,550 A | 9/1987 | Engbert et al. | |
| 5,326,903 A | 7/1994 | Shimasaki et al. | |
| 5,731,458 A | 3/1998 | Dahmer et al. | |
| 5,883,291 A | 3/1999 | Schleenstein et al. | |
| 2004/0068137 A1 | 4/2004 | Herold et al. | |
| 2005/0154227 A1 | 7/2005 | Stroefer et al. | |
| 2011/0178329 A1 | 7/2011 | Bock et al. | |
| 2011/0207961 A1 | 8/2011 | Geissler et al. | |
| 2011/0313192 A1 | 12/2011 | Rosendahl et al. | |

FOREIGN PATENT DOCUMENTS

| | | |
|---|---|---|
| DE | 199 07 648 | 8/2000 |
| EP | 0 078 005 | 5/1983 |
| EP | 0 092 738 | 11/1983 |
| EP | 0 555 628 | 8/1993 |
| EP | 0 795 543 | 9/1997 |
| EP | 1 403 248 | 3/2004 |
| WO | 03 074477 | 9/2003 |
| WO | 2011 015541 | 2/2011 |
| WO | 2011 036062 | 3/2011 |
| WO | 2011 051314 | 5/2011 |

OTHER PUBLICATIONS

Saunders, J.H., et al., "Polyurethanes Chemistry and Technology," Internscience Publishers, p. 146, (1962).
International Search Report Issued Feb. 17, 2011 in PCT/EP10/68500 Flied Nov. 30, 2010.

* cited by examiner

*Primary Examiner* — Brandon Fetterolf
*Assistant Examiner* — Ana Z Muresan
(74) *Attorney, Agent, or Firm* — Oblon, Spivak, McClelland, Maier & Neustadt, L.L.P.

(57) ABSTRACT

A process is proposed for preparing isocyanates by thermally cleaving carbamates to obtain a carbamate cleavage gas comprising the corresponding isocyanate and the corresponding alcohol, which comprises quenching the carbamate cleavage gas in the presence of an ether which functions as an inhibitor for the reverse reaction of the isocyanate with the alcohol.

18 Claims, No Drawings

PROCESS FOR PREPARING ISOCYANATES BY THERMALLY CLEAVING CARBAMATES

CROSS REFERENCE TO RELATED APPLICATION

This application is a 371 of PCT/EP2010/068500, filed on Nov. 30, 2010, and claims priority to European Patent Application No. 09177643.5, filed on Dec. 1, 2009.

The invention relates to a process for preparing isocyanates by thermally cleaving carbamates, also known as carbamic esters or urethanes.

Carbamate cleavage is gaining increasing significance as a phosgene-free process for preparing isocyanates. Different apparatus has been proposed for industrial performance of the carbamate cleavage, more particularly columns (in EP 0 795 543), fluidized bed reactors (in EP 555 628 and in DE 199 07 648), and falling-film or thin-film evaporators (in EP 0 092 738). The carbamate cleavage can be conducted in the liquid phase or in the gas phase.

A problem in the thermal cleavage of carbamates is the formation of high molecular weight secondary components which arise through further reaction of the cleavage products. These can lead to deposits in the apparatus, and hence restrict continuous operation and lead to yield losses. The residues comprise especially allophanates and isocyanurates.

In order to avoid these problems, the isocyanate and alcohol cleavage products from the carbamate cleavage gas have to be separated from one another as rapidly as possible.

It is additionally known that the problem of the reverse and further reactions in the cleavage can be reduced by performing the carbamate cleavage in the presence of solvents since the reaction rate of the reverse reaction of isocyanate and alcohol (urethanization) and also the further reactions are known to be dependent on the solvent and the dilution by the solvent.

For example, J. H. Saunders and K. C. Frisch: Polyurethanes, Chemistry and Technology, 1962, p. 146, table 10, gives information about the reactivity of isocyanates with alcohols in the presence of different solvents. Diluting the carbamate cleavage products with an inert solvent suppresses the formation of high molecular weight conversion products; at the same time the solvent serves to discharge these secondary components and apparatus fouling is reduced.

Suitable solvents are especially high boilers, i.e. liquids whose boiling points under process conditions are at least 10° C., especially at least 20° C., above the boiling points of the cleavage products of the carbamate cleavage.

EP-B 0 795 543 describes particularly suitable high-boiling solvents for thermally cleaving carbamates, which have a defined boiling point or else a narrow boiling range, and which can be obtained as a distillation cut from thermally stable liquids selected from the group of the ortho, meta and para isomers of phenoxydiphenyl. Use of such solvents in the thermal cleavage of carbamates in columns can reduce the bottom temperature of the column with the same cleavage performance and unchanged mean temperature in the reaction section, which significantly reduces the formation of by-products and cracking products in the column bottoms. Disadvantages of this process are the fact that cleavage and cleavage gas separation are performed in the same apparatus, that the alcohol is used as a return stream at the top of the column, and that phenoxybiphenyl is barely commercially available and is thus expensive.

It is also known that the rate of urethane formation can be reduced by adding inhibitors. Examples of known inhibitors of urethane formation are hydrochloric acid, benzoyl chloride or p-toluenesulfonic acid (cf. Örtel: Polyurethane, $2^{nd}$ edition, 3.4.2, p. 92).

It was accordingly an object of the invention to provide an improved process for thermally cleaving carbamates in the presence of an additive, which leads to a reduced amount of residue with reduced specific energy costs.

The object is achieved by a process for preparing isocyanates by thermally cleaving carbamates to obtain a carbamate cleavage gas comprising the corresponding isocyanate and the corresponding alcohol, which comprises quenching the carbamate cleavage gas in the presence of an ether which functions as an inhibitor for the reverse reaction of the isocyanate with the alcohol.

It has been found that it is possible, by using ethers which function as inhibitors for the reverse reaction of the isocyanate with the alcohol, which are formed in the carbamate cleavage, to reduce the rate of the reverse reaction and hence to reduce the problems associated with the formation of secondary components. Compared to the use of pure solvents as additives, however, a significantly reduced specific amount of inhibitor is required therefor. More particularly, this also makes the removal and recovery of the additive more economically viable compared to additives which function merely as solvents.

According to the invention, the inhibitors used, which slow the reverse reaction of the isocyanate with the alcohol from the carbamate cleavage gas, are ethers.

It is assumed that ether binds the alcohol through the formation of hydrogen bonds, such that it is available for the reverse reaction only to a reduced degree, if at all.

The ether used is preferably a polyalkylene glycol dialkyl ether and/or a polyalkylene glycol diaryl ether.

Further preferably, the polyalkylene glycol dialkyl ether is a polyethylene glycol dialkyl ether. More preferably, the polyethylene glycol dialkyl ether used is diethylene glycol dimethyl ether, triethylene glycol dimethyl ether or tetraethylene glycol dimethyl ether.

The ether used is more preferably tetraethylene glycol dimethyl ether.

Further preferably, the ether used is polypropylene glycol dialkyl ether and/or polypropylene glycol diary ether.

The polypropylene glycol dialkyl ether used is preferably one or more substances selected from the following list: dipropylene glycol dimethyl ether, tripropylene glycol dimethyl ether or tetrapropylene glycol dimethyl ether.

In a further embodiment, cyclic or aromatic ethers/polyethers are used, preferably one or more substances selected from the following list: oxolane, dioxolane, trioxolane, diaryl ether, alkyl aryl ether, diphenyl ether, ditolyl ether and dibenzyl ether.

The carbamates which are supplied to the cleavage are especially N,N'-tolylenebis(O-alkylurethane), N,N'-tolylenebis(O-alkoxalkylurethane), N,N'-tolylenebis(O-arylurethane), N,N'-1,5-naphthalenebis(O-dialkylurethane), N,N'-1,5-naphthalenebis(O-alkoxylalkylurethane), N,N'-1,5-naphthalenebis(O-arylurethane), hexamethylenebis(O-alkylurethane), hexamethylenebis(O-alkoxyalkylurethane), isophoronebis(O-alkylurethane), isophoronebis(O-alkoxyalkylurethane), 4,4'-diphenylmethanedi-O-alkylurethane or 4,4'-diphenylmethanedi-O-alkoxyalkylurethane.

The ether used as an additive to the thermal cleavage may preferably be a high boiler, i.e. a substance which has a boiling point under operating conditions which is higher than the boiling points of the isocyanate and of the alcohol from the carbamate cleavage gas.

In a further embodiment, an ether which is an intermediate boiler is used, i.e. which has a boiling point under process conditions between the boiling point of the isocyanate and the alcohol.

In a further embodiment, the additive used in the thermal cleavage is an ether which has a boiling point below the boiling points of the alcohol and of the isocyanate from the carbamate cleavage gas, i.e. a low boiler.

Quenching is known to mean the rapid cooling of a gas with a liquid. In the present context, quenching is understood to mean, more particularly, cooling of the carbamate cleavage gas within less than 10 seconds with a large amount of an ether which is liquid under the operating conditions of the thermal cleavage.

After the contact phase of the carbamate cleavage gas with the liquid additive, which is an ether, the alcohol and isocyanate components from the carbamate cleavage gas are separated from one another in the quench apparatus within a period of less than 200 seconds. The task of the quench apparatus thus consists in quenching the carbamate cleavage gas and separating the isocyanate and alcohol components from one another, especially by rectification.

For this purpose, very rapid, virtually instantaneous cooling of the carbamate cleavage gas is carried out.

The quench process stage can be performed at an operating pressure in the range from 0.001 to 20 bar absolute.

The quench process stage is preferably performed under reduced pressure in the range from 1 to 100 mbar abs.

By virtue of an ether which functions as an inhibitor for the reverse reaction of the isocyanate with the alcohol being used in accordance with the invention as an additive in the thermal cleavage of carbamates, it is possible to greatly suppress the formation of by-products, especially the allophanate formation, with a specifically smaller amount of additive.

More preferably, a mixture of the carbamate cleavage gas and the ether is supplied to the quench process stage.

This mixture preferably comprises 0.1 to 20 mol of ether/mol of alcohol.

The mixture comprising the carbamate cleavage gas and the ether which is supplied to the quench process stage preferably has a temperature in the range from 150 to 500° C. and is advantageously decompressed into the apparatus in which the quench process stage is performed.

The thermal cleavage of the carbamate is preferably performed in a reactor at a temperature in the range from 150 to 500° C.

Further preferably, the quench process stage may be preceded upstream by a gas cooler which cools the carbamate cleavage gas down to the condensation limit thereof.

It is advantageous to perform the carbamate cleavage in a fluidized bed, which is especially operated under reduced pressure.

The quench process stage is preferably performed in an apparatus which enables very rapid cooling (quenching) with the liquid ether, especially a Venturi quench, a jet quench, a pipe quench, a vortex quench or a rotary quench, with a quench column connected downstream, in which the quenched carbamate cleavage gas is separated rectificatively. The total residence time of the carbamate cleavage gas in the quench process stage, i.e. during the rapid cooling and rectificative separation of the cooled carbamate cleavage gas, is advantageously less than 200 seconds.

The column is preferably operated at low liquid holdup, the liquid holdup especially being less than 6% thereof. The residence time resulting from the liquid volume backed up in the quench column is crucially influenced by the liquid velocity of the quench medium. The superficial velocity—also referred to as trickle density—i.e. the liquid velocity based on the column cross section, is preferably <20 m³/m²h and more preferably <10 m³/m²h. The lower limit results from the operating range of the column internals used and is approx. 0.2 m³/m² h.

The operating state of the quench column, characterized by the formula $\rho_{gas}^{0.5} \cdot u_{gas}$ [Pa$^{0.5}$] is preferably set within the range from 0.5 to 2.

In a further embodiment, the quench process stage is performed in a column, and gaseous hydrogen chloride is fed into the bottom of the column in addition to the inert or inhibiting solvent, to inhibit the reverse reaction of the isocyanate with the alcohol.

The invention is illustrated in detail hereinafter by working examples.

For this purpose, the reaction rate of the urethanization of 2,4-tolylene diisocyanate (2,4-TDI) with isobutanol was examined in different solvents. As is well known, the reaction has second-order kinetics and the reaction rate depends on the alcohol concentration.

First, the reaction rate of the urethanization of 2,4-TDI in an ether which is used in the process according to the invention was examined:

WORKING EXAMPLE ON THE LABORATORY SCALE (INVENTIVE)

Urethanization of 2,4-TDI in Tetraethylene Glycol Dimethyl Ether (Tetraglyme)

A 250 ml four-neck flask with Teflon paddle stirrer, dropping funnel, thermometer, condenser and heating bath was purged with argon. 88.70 g (0.40 mol) of tetraglyme and 17.40 g (0.10 mol) of 2,4-TDI were initially charged in the reactor and heated to 40° C. A zero sample was taken, and 14.79 g (0.20 mol) of isobutanol were metered in at 400 rpm within 0.5 min. The isocyanate content was monitored by sampling as a function of time, and the $2^{nd}$ order kinetic constant was determined.

Table 1 below shows the decrease in the isocyanate content as a function of time.

TABLE 1

| T [min] | NCO [% by wt.] | T [° C.] |
| --- | --- | --- |
| 0 | 6.9 | 40 |
| 2 | 6.7 | 39 |
| 4 | 6.5 | 42 |
| 30 | 4.9 | 42 |

Comparative Example on the Laboratory Scale

Urethanization of 2,4-TDI in Chlorobenzene

For comparison, the same reaction was carried out in the same way in the same apparatus, except, in a departure from the above experiment, in chlorobenzene as the solvent. To this end, 69.70 g (0.62 mol) of chlorobenzene were initially charged with 17.40 g (0.10 mol) of 2,4-TDI in the reactor, which had been purged beforehand with argon, and heated to 40° C. A zero sample was taken, and 14.79 g (0.20 mol) of isobutanol were metered in at 400 rpm within 0.5 minute. The isocyanate content was monitored by sampling as a function of time, and the $2^{nd}$ order kinetic constant was determined. The decrease in the isocyanate content in percent by weight in the first few minutes and at the end of the experiment as a function of time is shown in table 2 below:

TABLE 2

| T [min] | NCO [% by wt.] | T [° C.] |
|---------|----------------|----------|
| 0       | 8.2            | 40       |
| 2       | 5.6            | 47       |
| 4       | 4.8            | 47       |
| 30      | 3.2            | 41       |

The comparison of the decreases in the iscocyanate content shown in tables 1 and 2 shows that the decrease in the isocyanate content in the presence of the chlorobenzene solvent (comparative example), especially in the first four minutes, is significant and is about 41%. In contrast, the isocyanate content in the inventive example, i.e. in the presence of tetraglyme, decreases only by 4%.

Fitting of the second-order rate constants via least mean squares regression with the Presto kinetics program shows that the rate constant for the reaction in the presence of tetraglyme (working example according to the invention) is only approx. 7% of the rate constant for the comparative example (in the presence of chlorobenzene).

The significant temperature difference of the two reaction mixtures also shows the different reactivity depending on the solvent used.

A working example for the performance of the process according to the invention in a quench column is described hereinafter.

Working Example on the Industrial Scale

In a cleavage apparatus, 2,4-tolylenebis(O-isobutyl carbamate) is cleaved continuously and then quenched. The cleavage is effected at 400° C. with a fluidized bed. The cleavage gas thus obtained is cooled, before it is introduced into the quench.

An austenitic steel column with 6 theoretical plates and a diameter of 60 mm is equipped with a sheet metal packing with low liquid holdup, in order to minimize the residence time. The product of $\rho_{gas}^{0.5} \cdot u_{gas}$ in the column varies within the range from 0.5 to 1.7 $Pa^{0.5}$, where $u_{gas}$=superficial velocity of the ascending gas, $\rho_{gas}$=density of the ascending gas. The quench is operated at 30 mbar. The trickle density is approx. 7 $m^3/m^2 h$.

53.9 mol/h of a cleavage gas comprising 58 mol % of butanol and 28.7 mol % of 2,4-TDI (residual $N_2$ as fluidization gas) are introduced in gaseous form at 280° C. to the $2^{nd}$ stage of the carbamate cleavage gas quench. At the top of the column, 81.0 mol/h of tetraglyme are introduced in liquid form at 20° C. to the distributor. At the top of the column, a gaseous stream of 38.3 mol/h is drawn off. At the top, 31.1 mol/h of isobutanol is found. The proportion of tetraglyme in the tops is 0.05 mol/h.

At the bottom of the column, 96.5 mol/h are drawn off at 155° C. 15.4 mol/h of 2,4-TDI are found therein.

The proportion of allophanates and isocyanurates at the bottom of the column is less than 2 mol % based on 2,4-TDI.

The invention claimed is:

1. A process for preparing an isocyanate, comprising:
   thermally cleaving a carbamate to obtain a carbamate cleavage gas comprising an isocyanate and an alcohol, and
   quenching the carbamate cleavage gas in the presence of an ether, wherein the ether inhibits a reverse reaction of the isocyanate with the alcohol, wherein
   the ether is a polyalkylene glycol dialkyl ether, a polyalkylene glycol diaryl ether, or both.

2. The process of claim 1, wherein the ether is a polyethylene glycol dialkyl ether.

3. The process of claim 2, wherein the polyethylene glycol dialkyl ether is at least one ether selected from the group consisting of diethylene glycol dimethyl ether, triethylene glycol dimethyl ether and tetraethylene glycol dimethyl ether.

4. The process of claim 3, wherein the ether is tetraethylene glycol dimethyl ether.

5. The process of claim 1, wherein the ether is a polypropylene glycol dialkyl ether, a polypropylene glycol diaryl ether, or both.

6. The process of claim 5, wherein the ether is selected from the group consisting of dipropylene glycol dimethyl ether, tripropylene glycol dimethyl ether and tetrapropylene glycol dimethyl ether.

7. The process of claim 1, wherein the carbamate is at least one selected from the group consisting of N,N'-tolylenebis(O-alkylurethane), N,N'-tolylenebis(O-alkoxalkylurethane), N,N'-tolylenebis(O-arylurethane), N,N' -1,5-naphthalenebis(O-dialkylurethane), N,N'-1,5-naphthalenebis(O-alkoxylalkylurethane), N,N'-1,5-naphthalenebis(O-arylurethane), hexamethylenebis(O-alkylurethane), hexamethylenebis(O-alkoxyalkylurethane), isophoronebis(O-alkylurethane), isophoronebis(O-alkoxyalkylurethane), 4,4,' -diphenylmethanedi-O-alkylurethane and 4,4' -diphenylmethanedi-O-alkoxyalkylurethane.

8. The process of claim 1, wherein a mixture of the carbamate cleavage gas and the ether is supplied to the quenching process stage.

9. The process of claim 8, wherein the mixture of the carbamate cleavage gas and the ether comprises 0.1 to 20 mol of ether per mole of alcohol.

10. The process of claim 8, wherein the mixture of the carbamate cleavage gas and the ether has a temperature of 150 to 500° C. and is decompressed when supplied to the quenching process stage.

11. The process of claim 1, wherein the thermal cleavage of the carbamate is performed in a reactor at a temperature of 150 to 500° C.

12. The process of claim 1, further comprising
    prior to the quenching process stage, cooling the carbamate cleavage gas to a condensation limit thereof in a gas cooler.

13. The process of claim 1,
    wherein a total residence time in the quenching process stage is less than 200 seconds.

14. The process of claim 1,
    wherein
    a liquid holdup in an apparatus in which the quenching process stage is performed is less than 6% of a superficial cross section thereof.

15. The process of claim 1,
    wherein
    an operating state of an apparatus in which the quenching process stage is performed is characterized by a formula $$\rho_{gas}^{0.5} \cdot u_{gas}$$

in which
$\rho$ is a density of the carbamate cleavage gas and
$u$ is a velocity of the carbamate cleavage gas in the apparatus in which the quenching process stage is performed, and the product $\rho_{gas}^{0.5} \cdot u_{gas}$ has a value in a range from 0.5 to 2.

16. The process of claim 1,
    wherein
    a superficial velocity in a column is less than 20 $m^3/m^2$ h.

17. The process of claim 1,
    wherein the quenching process stage is performed in a column, and gaseous hydrogen chloride is fed into a bottom of the column which inhibits the reverse reaction of the isocyanate with the alcohol.

18. The process of claim 1, wherein
a superficial velocity in the column is less than $10\,m^3/m^2\,h$.

* * * * *